Figure 1:
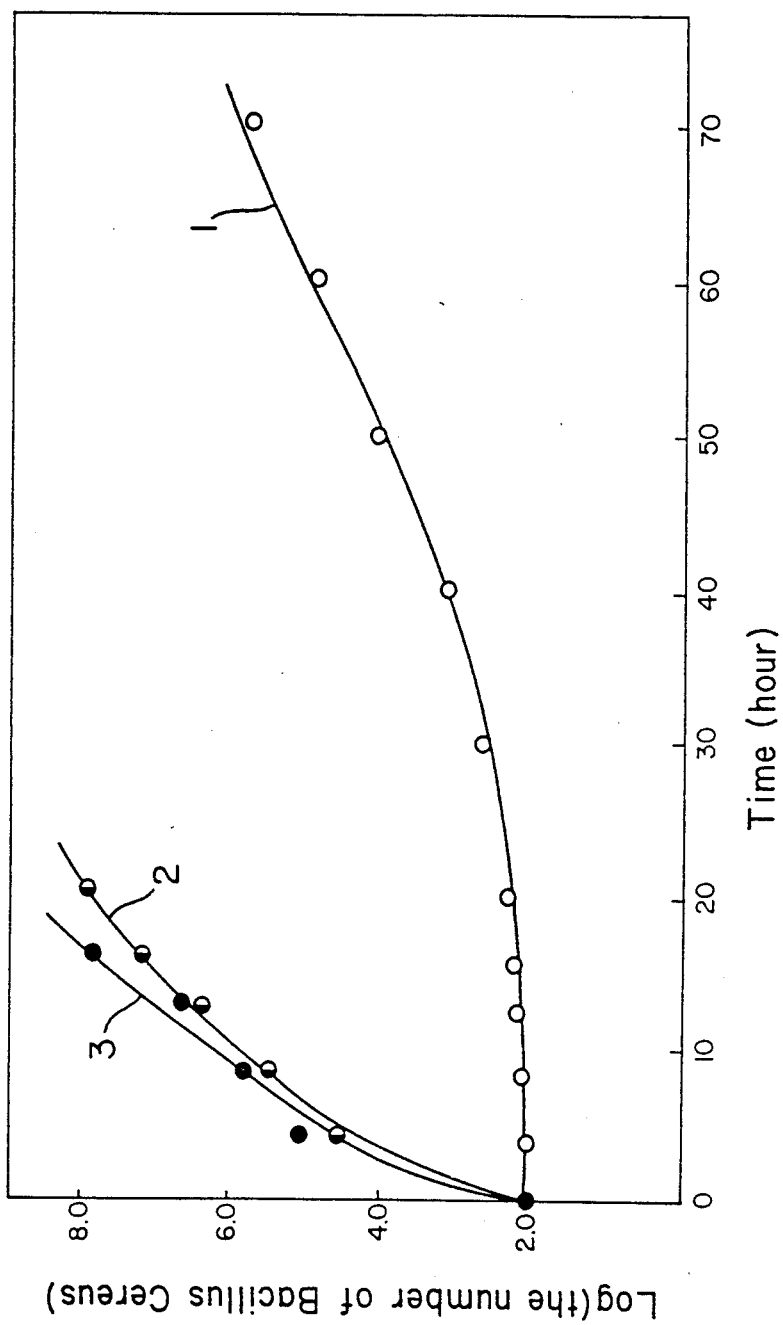
Figure 2:
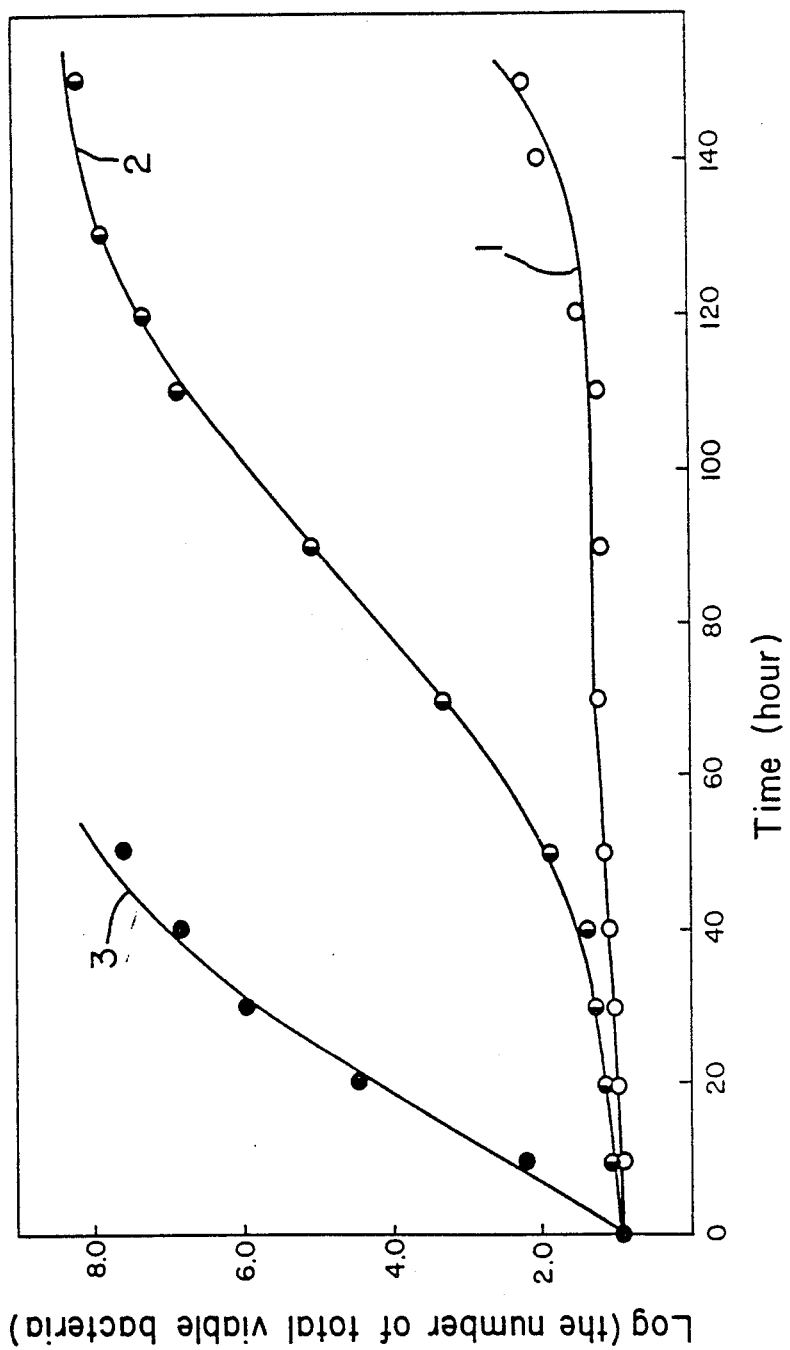

United States Patent [19]

Ueno et al.

[11] Patent Number: 4,954,358

[45] Date of Patent: Sep. 4, 1990

[54] **MULTIPLICATION INHIBITOR FOR *BACILLUS CEREUS***

[75] Inventors: Ryuzo Ueno; Yatsuka Fujita; Munemitsu Yamamoto; Hiroshi Kozakai, all of Nishinomiya, Japan

[73] Assignee: Kabushiki Kaisha Ueno Seiyaku Oyo Kenkyujo, Osaka, Japan

[21] Appl. No.: 128,557

[22] Filed: Dec. 3, 1987

[30] Foreign Application Priority Data

Dec. 4, 1986 [JP] Japan ............ 61-289715

[51] Int. Cl.5 ............ A21D 4/00; A61K 37/08

[52] U.S. Cl. ............ 426/331; 426/321; 426/335; 530/358; 514/21

[58] Field of Search ............ 426/321, 331, 335; 514/21; 530/358

[56] References Cited

U.S. PATENT DOCUMENTS 3,917,816 11/1975 Yueh ............ 424/61

4,749,689 6/1988 Miyata et al. ............ 514/21

FOREIGN PATENT DOCUMENTS

| | | | |
|---|---|---|---|
| 0002603 | 1/1980 | Japan | 530/358 |
| 0002612 | 1/1980 | Japan | 530/358 |
| 0002613 | 1/1980 | Japan | 530/358 |
| 55-2613 | 1/1980 | Japan | 530/358 |
| 0219363 | 9/1986 | Japan | 530/358 |
| 0473720 | 6/1975 | U.S.S.R. | 530/358 |

OTHER PUBLICATIONS

Gerasimene et al., "Phospholipase of *Bacillus cereus*", Biological Abstracts, vol. 63, p. 2575, 1977.

*Primary Examiner*—Margaret Moskowitz
*Assistant Examiner*—Abdel A. Mohamed
*Attorney, Agent, or Firm*—Wegner & Bretschneider

[57] ABSTRACT

The present invention provides a new inhibitor for *Bacillus cereus* which has been designated officially as a pathogen of food poisoning, which comprises a protamine or its salt as an essential component.

13 Claims, 2 Drawing Sheets

MULTIPLICATION INHIBITOR FOR BACILLUS CEREUS

BACKGROUND OF THE INVENTION

The present invention relates to a multiplication inhibitor for Bacillus cereus which is one kind of the cytotoxic bacteria causing bacterial food poisoning.

Nowadays people are increasingly being endangered by bacterial food poisoning in the way of food where, in keeping with progress in packing and food processing techniques for preservation besides development in means of transportation, revolutionary improvement of the distribution systems, etc., consumers are being supplied with a great variety of prepared assorted foods such as packed lunches, sandwiches, hot dogs, and cooked foods in addition to traditional processed foods such as fish paste products, processed meat, and soybean products, for example, miso and soy sauce. Recently, a frequent incidence of food poisoning caused by Bacillus cereus has come to the fore. Therefore, said cytotoxic bacterium has newly been designated officially as a pathogen of food poisoning, but there has not yet been discovered any effective means to prevent the incidence of the related poisoning.

SUMMARY OF THE INVENTION

The conventional synthetic preservatives which are used for traditional processed foods are not permitted to be applied to prepared assorted foods, and prevention of deterioration of foods by general bacteria and improvement of the keeping quality are practiced by addition of amino acids, fatty acid esters, phosphates, organic acids, alcohols, etc. Such additives, however, have been hardly recognized as effective in inhibiting the growth and multiplication of Bacillus cereus in the practical application to foods.

On the other hand, the influence of Bacillus cereus upon the appearance of food is not noticeable as compared with general putrefying bacteria. A piece of food which does not show putrefaction outwardly may have allowed Bacillus cereus to propagate and heavily contaminate the food, contact with this spoiled food leading to cytotoxism.

The object of the present invention is to provide a new inhibitor for Bacillus cereus, which contains a protamine or salts thereof as an active ingredient.

BRIEF DESCRIPTION OF DRAWINGS

FIG. 1 diagrammatically shows the change of the bacterial number of Bacillus cereus at 30° C. with time in a test using cooked rice contaminated with said bacteria.

FIG. 2 likewise shows the bacterial number of general active bacteria at 30° C. with time in a test using cooked rice not contaminated with Bacillus cereus.

DETAILED DESCRIPTION OF THE INVENTION

The present invention relates to a multiplication inhibitor for Bacillus cereus, which comprises a protamine or salts thereof as an active ingredient.

The protamine used for this invention is a strongly basic protein having a high arginine content and a relatively low molecular weight, and a source is a nucleoprotamine in which it is present in combination with a deoxyribonucleic acid, existing in a spermatozoid nucleus of a vertebrate animal such as a fish (for example, salmon, trout, herring and mackerel) or a cock. This protamine can be obtained by any of the prior art methods (refer, for example, to Japanese patent application KOKAI No. 320/1980, Japanese Patent Publication No. 31518/1984, Japanese patent application Nos. 29748/1986, 29746/1986, 29747/1986, and 29745/1986).

A protamine dealt with in the present invention can be obtained by a prior art technique, according to which, for example, as described in said Japanese patent application KOKAI No. 320/1980 and Japanese Patent Publication No. 31518/1984 milt, etc. of fish is treated with a mineral acid and the nucleoprotamine contained therein is hydrolyzed for the extraction. A protamine obtained by such a method is a salt of a mineral acid (sulfuric acid, hydrochloric acid, or the like). Such a salt of a mineral acid can be used as it is for the present invention or a protamine base which is obtainable by removal of the mineral acid can also be used. Acids used to neutralize a protamine are, for example, inorganic acids, such as sulfuric acid, hydrochloric acid and phosphoric acid and organic acids, such as acetic acid, lactic acid and methyl hydrogen sulfate. The effect is almost the same irrespective of which protamine is used. Free protamines and their salts will hereinafter be referred to simply as protamine unless otherwise stated.

In using a protamine, its basic characteristics must be considered in relation to the kind, etc. of the food to which it is applied. For example, the antibacterial effect of a protamine is more conspicuous when the pH of the medium indicates alkalinity; the antibacterial effect of a protamine differs depending on the ingredients in the medium; and a protamine is relatively stable to heat and has high resistance to denaturation by heating.

In the practice of the present invention, it is practical for a multiplication inhibitor for Bacillus cereus to contain other additives, for example, one kind of substance or more selected as desired from among the groups comprising emulsifying agents for foods, organic acids and their salts, alcohols, phosphoric acids, lysozyme, amino acids, sorbic acid and its salts, and benzoic acid and its esters glycorrhiza extracted antibacterials, chitosan and its lightly decomposed materials. In addition to the above additives other food-additives such as sweetening agents, seasonings, flavorings, coloring agents, antioxidants, excitonurients, quality-improving agents and the like.

Useful as said emulsifying agents for foods in this invention are, for example, glycerol fatty acid ester, saccharose fatty acid ester, sorbitan fatty acid ester, polyoxyethylene sorbitan fatty acid ester, propylene glycol fatty acid ester, and lecithin.

Useful as said organic acids or their salts are, for example, citric acid, gluconic acid, acetic acid, tartaric acid, lactic acid, fumaric acid, succinic acid, malic acid, adipic acid, and ascorbic acid, including their sodium salts, calcium salts, and ferric/ferrous salts.

Useful as said alcohols are, for example, ethylalcohol. glycerol, propylene glycol, polyethylene glycol, and benzylalcohol.

Useful as said phosphoric acids are, for example, phosphoric acid, pyrophosphoric acid, polyphosphoric acid, and hexametaphosphoric acid, including their sodium salts and potassium salts.

Useful as said amino acids are, for example, neutral amino acids; such as glycine, alanine, valine, leucine, isoleucine, phenylalanine, proline, serine, threonine, cysteine, mystine, methionine, tryptophane, thyrosine, hydroxyproline, asparagine, and glutamine; basic amino acids, such as lysine, arginine, and histidine; and acid amino acids, such as aspartic acid and glutamic acid. Especially preferable are neutral amino acids and basic amino acids such as glycine, alanine, valine, leucine, phenylalanine, methionine, tryptophane, asparagine, glutamine, lysine, and arginine.

Useful as said glycyrrhira, extracted antibacterials are, for example, antibacterials prepared according to a process as described in Japanese Patent Publication.-(KOKAI) No. 172928/1985.

Useful as said chitosan and its lightly decomposed materials are one prepared according to Japanese Patent Publication (KOKAI) No. 83877/1987.

Among the aforementioned additives the emulsifying agents organic acids or their salts, alcohols, phosphoric acids, lysozymes, amino acids, sorbic acids or their salts, benzoic acids or their esters strengthen the effect of the protamine in comparison with the sole use of the protamine. Therefore, these additives are preferably co-used with protamine as a multiplication inhibitor for Bacillus cereus.

The present invention is useful in application broadly to general processed foods covering not only processed foods produced primarily from cereals, vegetables, and fruit, but also those of animal proteins, fish products, and meat. Whereas no special restriction applies to the amount of addition of the protamine, it is preferable to adjust the addition to 0.001%-2%, or more preferably to 0.003%-0.5%, in terms of protamine in consideration of the antibacterial effect, the influence upon people's liking for the food, and the like. When an amino acid is used in combination with a protamine, it is preferable to adjust the addition of the protamine to 0.001%-2%,or more preferably to 0.01%-0.5%, in consideration of the antibacterial effect. An amino acid can be added in any quantity that does not affect the taste or flavor of the food. Accordingly, an amino acid is used in a proportion within 0.001-1,000 parts by weight, or preferably within 0.02~200 parts by weight, against 1 part by weight of protamine. If the food contains a substantially large amount of amino acid prior to the antibacterial treatment, the addition of amino acid can be reduced proportionately.

When an emulsifying agent for foods is used in combination with a protamine, the same condition as when an amino acid is added applies to the addition of the protamine. The emulsifying agent for foods can be added at any quantity that does not affect the taste, flavor, etc. of the food. An emulsifying agent for foods can be used in a proportion within the range of 0.0001-500 parts by weight, or preferably within the range of 0.002-50 parts by weight, against 1 part by weight of protamine.

For the same reason as above, an organic acid or its salt is added to a protamine in a proportion of 0.001~1,000 parts by weight, or preferably in a proportion of 0.02 -100 parts by weight, against 1 part by weight of protamine. If the food already contains an organic acid or its salt, the addition of an organic acid or its salt can be reduced proportionately.

When lysozyme is used in combination with protamine, the lysozyme is added in a proportion within the range of 0.001-1,000 parts by weight, or preferably within the range of 0.02-200 parts by weight, against 1 part by weight of protamine. The same reason as above applies.

When a phosphate is used in combination with a protamine, the phosphate is used in a proportion within the range of 0.001-500 parts by weight, or preferably within the range of 0.02-50 parts by weight, against 1 part by weight of protamine. The same reason as above applies.

When an alcohol is used in combination with a protamine, the alcohol is used in a proportion within the range of 0.01-1,000 parts by weight, or preferably 0.2~200 parts by weight, against 1 part by weight of protamine. The same reason as above applies.

If the food already contains alcohol, the amount of alcohol contained in the food can be included in the amount of alcohol to be added. That is, if a food already contains alcohol in a sufficient amount to promote the activity of the protamine, additional amounts of alcohol need not be added to the food, but if the food contains insufficient alcohol to promote the effect of the protamine, additional alcohol is added to make up the amounts in the food described above.

When sorbic acid, benzoic acid or the like is used in combination with a protamine, such an acid is used as a free acid in a proportion within the range of 0.001~100 parts by weight, or preferably within the range of 0.01~50 parts by weight, against 1 part by weight of protamine. The same reason as above applies.

In the practice of this invention, the protamine as well as additives used in combination therewith may be added to the food at any step of the production procedure of the food. The addition may be achieved individually or simultaneously by blending them at the production of a processed food, or spraying or immersing the food, a food receptacle, a packing material and the like into a solution thereof. The mixture of the protamine and the additives may be formed into any drug shape which does not adversely affect the workability at addition and dispersability into the foods. The protamine may be desirable mixed with one or more additives selected from the group consisting of emulsifying agents, organic acids or their salts, alcohols, phosphoric acids, lysozyme, amino acids, sorbic acids or their salts, benzoic acid and its salts at the aforementioned ratio. In case of powder drug dextrin, lactose, starch, wheat and the like may be additionally mixed so as to control the amount of protamine to be added against the food. Further, in case of a liquid drug the protamine may be desirably dissolved in water or an aqueous solution of ethanol (e.g. 5-85%) at the concentration of 1-10%.

EXAMPLE 1

Two hundred grams of polished rice was washed in water, and with the addition of 240 ml of water, it was cooked for approximately 15 minutes in an electric rice-cooker which was of the type in public use. The rice cooked was left standing in hot steam for 10 minutes, and then left to cool off at room temperature. On the other hand, a suspension of spores of Bacillus cereus was prepared and added to the cooked rice, which had cooled off, in the proportion of $n \times 10^2$ to 1 g final specimen. Specimens were prepared by mixing the rice evenly with addition of the spores.

The Bacillus cereus subjected to the test was of the type GH.1 in the H blood serum type grouping by Tailor et al. (reference: J. Med. Microbiol. Volume 3, P543, 1975).

The cooked rice was put in a plastic case for each 120 g and its temperature was maintained at 30° C., and the number of total viable bacteria and the number of Bacillus cereus were measured periodically using a standard agar culture medium (37° C., 48 hours) and a polymyxin BCW agar culture medium with 5% egg yellow (37° C., 24 hours) for each In parallel with this measurement of the bacterium number, the specimens were examined concerning the outward appearance and the possible smell of putrefaction.

The results of the measurement are shown in Table 1.

boiling for 30 minutes at 90° C., prepared into custard pudding.

On the other hand, specimens were prepared by planting in it spores of Bacillus cereus in suspension so as to make the bacterium number $n \times 10^2$ per 1 g final specimen (The same Bacillus cereus as in Test 1 was employed.)

The specimens thus prepared were cooled in running water for 30 minutes, left standing at 30° C., and mea-

TABLE 1

| | | Standing Time (hour) | | | | | | |
|---|---|---|---|---|---|---|---|---|
| Specimen | Test Item | 0 | 6 | 12 | 18 | 24 | 30 | 36 |
| *Bacillus Cereus,* unplanted specimen | Bacterium number | <10 | $2.1 \times 10^2$ | $7.0 \times 10^3$ | $5.6 \times 10^4$ | $4.9 \times 10^5$ | $3.2 \times 10^6$ | $3.2 \times 10^7$ |
| | Smell of putrefaction | | | No | | | Yes | |
| | Outward Appearance | | | Normal | | | ± | + |
| *Bacillus cereus,* planted specimen ($n \times 10^2$/g) | Bacterium number | $1.5 \times 10^2$ | $4.8 \times 10^5$ | $6.1 \times 10^6$ | $1.0 \times 10^7$ | $2.1 \times 10^7$ | $8.9 \times 10^7$ | $1.2 \times 10^8$ |
| | Smell of putrefaction | | | No | | | Yes | |
| | Outward Appearance | | | Normal | | | ± | + |

±: Slightly softened
+: Softened

According to the results, when Bacillus cereus is not planted, the putrefaction of the specimen is clearly recognized, smelling of putrefaction and softening in outward appearance, after 30 hours of standing time when the bacterium number reaches $3.2 \times 10^6$.

When Bacillus cereus is planted, the bacterium number reaches $6.1 \times 10^6$, at which food poisoning is possible, after 12 hours. The specimen begins to smell of sured periodically, as in Test 1, concerning the total viable bacterium number and the bacterium number of Bacillus cereus.

In parallel with this measurement, the specimens were examined concerning the outward appearance when the heat seal is removed and possible smell of putrefaction.

The results are shown in Table 2.

TABLE 2

| | | Standing Time (hour) | | | | | | |
|---|---|---|---|---|---|---|---|---|
| Specimen | Test Item | 0 | 6 | 12 | 18 | 24 | 30 | 36 |
| *Bacillus Cereus,* Unplanted specimen | Bacterium number | <10 | $2.5 \times 10$ | $3.9 \times 10^3$ | $6.8 \times 10^4$ | $4.7 \times 10^6$ | $5.9 \times 10^7$ | $1.4 \times 10^8$ |
| | Smell of putrefaction | | | No | | | Yes | |
| | Outward Appearance | | | | Normal | | | Texture softens |
| *Bacillus cereus,* Planted specimen ($n \times 10^2$/g) | Bacterium number | $1.1 \times 10^2$ | $2.9 \times 10^5$ | $7.2 \times 10^6$ | $2.5 \times 10^7$ | $6.1 \times 10^7$ | $3.8 \times 10^8$ | $5.6 \times 10^8$ |
| | Smell of putrefaction | | | No | | | Yes | |
| | Outward Appearance | | | | Normal | | | Texture softens | putrefaction and soften in outward appearance after 30 hours from the beginning and when the bacterium number reaches $8.9 \times 10^7$. It is clear from the above that, when Bacillus cereus is planted, Bacillus cereus reaches a state where food poisoning is possible in advance of the putrefaction.

The results of the test clarify the mechanism of causing food poisoning in which, when food is contaminated by Bacillus cereus, no change is recognized concerning the outward appearance and possible smell of putrefaction at the point where the food has reached a state in which food poisoning is possible, and the putrefaction is not observed until the rotting bacterium reaches more than $10^6$.

EXAMPLE 2

Into 970 ml of milk warmed at 40° C. was added 550 g of whole egg well stirred and 220 g of sugar well dissolve. The milk was then strained and mixed uniformly. The liquid mixture was poured into a deep vessel (capacity: 250 ml), heat sealed, and, by steam- The results clarify, as in Example 1, the mechanism by which Bacillus cereus causes food poisoning.

EXAMPLE 3

The minimum growth inhibiting concentration (MIC) of various antibacterial substances against Bacillus cereus and other general putrefying bacteria were measured by using a standard nutrient agar (made by Difco Corp.) and by introducing the agar plate dilution method.

On a plain culture medium on which chemicals were placed in a stepwise dilution system the liquid spore suspension ($\times 10^8$/ml) with respect to the strains of the genus of Bacillus and the respective pre-culture mediums (37° C., 24 hours) provided by Brain Heart Infusion Broth with respect to the other strains were smeared.

Said bacterial liquids were cultured at 37° C. for 24 hours after the smearing and MIC was determined by judging with the naked eye whether there was growth of bacteria or not.

The results are shown in Table 3.

TABLE 3

| | Strain | | | | | | | | |
|---|---|---|---|---|---|---|---|---|---|
| Anti-bacterial substance | *Bacillus cereus* | *Bacillus subtilis* | *Bacillus coaglans* | *Bacillus licheniformis* | *Bacillus megaterium* | *Staphylococcus aureus* | *Leuconostoc mesenteroides* | *Lacto-bacillus casei* | *Streptococcus faecalis* |
| Glycine | >8.0 | 1.0 | 1.0 | 2.0 | 1.0 | 5.0 | 4.0 | 4.0 | 4.0 |

TABLE 3-continued

| Antibacterial substance | Bacillus cereus | Bacillus subtilis | Bacillus coaglans | Bacillus licheniformis | Bacillus megaterium | Staphylococcus aureus | Leuconostoc mesenteroides | Lactobacillus casei | Streptococcus faecalis |
| --- | --- | --- | --- | --- | --- | --- | --- | --- | --- |
| Caprylic acid Monoglyceride | 0.05 | 0.05 | 0.05 | 0.05 | 0.05 | 0.1 | 0.05 | 0.05 | 0.05 |
| Capric acid monoglyceride | 0.01 | 0.01 | 0.01 | 0.01 | 0.01 | 0.025 | 0.025 | 0.025 | 0.025 |
| Lauric acid monoglyceride | 0.0025 | 0.0025 | 0.0025 | 0.0025 | 0.0025 | 0.01 | 0.01 | 0.01 | 0.01 |
| Sodium pyrophosphate | >0.5 | >0.5 | >0.5 | >0.5 | >0.5 | >0.5 | >0.5 | >0.5 | >0.5 |
| Sodium polyphosphat | 0.5 | 0.025 | 0.5 | 0.025 | 0.025 | 0.5 | 0.5 | 0.5 | 0.5 |
| Sodium hexa-metaphosphate | 0.125 | 0.125 | 0.125 | 0.125 | 0.125 | 0.125 | 0.125 | 0.125 | 0.125 |
| sodium acetate | >0.5 | >0.5 | >0.5 | >0.5 | >0.5 | >0.5 | >0.5 | >0.5 | >0.5 |
| Lysozyme | >0.05 | 0.02 | 0.05 | >0.05 | 0.05 | >0.05 | >0.05 | >0.05 | >0.05 |
| protamine sulfate | 0.1 | 0.05 | 0.05 | 0.05 | 0.05 | 0.05 | 0.1 | 0.1 | 0.1 |
| Protamine hydrochloride | 0.1 | 0.05 | 0.05 | 0.05 | 0.05 | 0.05 | 0.1 | 0.1 | 0.1 |
| Free protaine | 0.1 | 0.05 | 0.05 | 0.05 | 0.05 | 0.05 | 0.1 | 0.1 | 0.1 |

EXAMPLE 4

Each of the chemicals shown in Table 4 was dissolved in 20 ml of water to form an aqueous solution of a set concentration. Each of these aqueous solutions was added to cooked rice which had been prepared and cooled at room temperature in the same manner as in Example 1. Following the same procedure as in Example 1, except that the rice and the chemicals were mixed well evenly, the bacterial numbers were measured and the time over which the rice kept unspoiled was determined (30° C.).

The results are shown in Table 4. The effective keeping time in the table means the time over which a specimen, which has not been contaminated with Bacillus cereus, keeps good without producing smell of putrefaction or change in outward appearance (the figure in the upper space for each chemical shows it), whereas it means the time after which a specimen, which has been contaminated with Bacillus cereus, shows a bacteria number of Bacillus cereus of $10^6$/g or more (the figure in the lower space for each chemical shows the time).

Note: In past cases of food poisoning caused by Bacillus cereus the bacteria number of Bacillus cereus was reported to be in the range of $10^6 \sim 10^8$/g.

FIG. 1 diagrammatically shows the change of the bacteria number of Bacillus cereus with time at 30° C., the specimen being cooked rice contaminated with Bacillus cereus.

FIG. 2 likewise shows the change of the bacteria number of total viable bacteria at 30° C. with time, the specimen being cooked rice not contaminated with Bacillus cereus.

(1) Free protamine was added in a quantity of 0.1%.

(2) Glycine was added in a quantity of 1%.

(3) No chemical was added.

TABLE 4

| Chemicals (concentration)[1] | Effective keeping time (hour) |
|---|---|
| Glycine | 110.0 |
| (1%) | 10.1 |
| Caprylic acid monoglyceride | 35.0 |
| (0.05%) | 8.6 |
| Capric acid monoglyceride | 35.0 |

TABLE 4-continued

| Chemicals (concentration)[1] | Effective keeping time (hour) |
|---|---|
| (0.01%) | 8.4 |
| Lauric acid monoglyceride | 40.0 |
| (0.01%) | 8.2 |
| Sodium pyrophosphate | 35.0 |
| (0.5%) | 8.6 |
| Sodium polyphosphate | 35.0 |
| (0.5%) | 9.0 |
| Sodium hexametaphosphate | 35.0 |
| (0.5%) | 9.2 |
| Sodium acetate | 43.0 |
| (0.4%) | 11.5 |
| Lysozyme | 35.0 |
| (0.05%) | 8.5 |
| Free protamine | >150 |
| (0.1%) | 72.6 |
| No addition | 40.0 |
| | 8.9 |

[1]Weight percent against the total weight of the specimen

EXAMPLE 5

Potato salad was prepared according to the following recipe.

| Materials | Proportions (g) |
|---|---|
| Potato (coarsely-crushed after boiling) | 300 |
| Carrot (chopped and then boiled) | 50 |
| Cucumber (sliced and then salted) | 70 |
| Onion (sliced and then salted) | 30 |
| Table salt | 2 |

Mayonnaise in the proportion of 10% by weight against the above materials was combined with various chemicals of prescribed concentrations listed in Table 5 and these were evenly mixed with the above food materials. Mixed specimens were prepared by inoculating Bacillus cereus in the form of a spore suspension in such a way as to make the bacterial number $n \times 10^2$ per gram on the final specimen.

The same Bacillus cereus as in Example 1 was employed for this example.

The potato salad thus prepared was packed into plastic containers and left standing at 30° C. The bacterial number of total viable active bacteria and that of Bacillus cereus were measured with respect to the changes with time by the same method as in Example 1.

The results are shown in Table 5. The effective keeping time and the figures in the upper and the lower spaces for each chemical in the list are used in the same meanings as in Example 4.

TABLE 5

| Chemicals (concentration)[1] | Effective keeping time (hour) |
| --- | --- |
| Glycine | 36.0 |
| (1%) | 12.0 |
| Sodium acetate | 27.0 |
| (0.4%) | 10.0 |
| Lauric acid monoglyceride | 22.0 |
| (0.01%) | 11.5 |
| Ethyl alcohol | 29.2 |
| (1.0%) | 10.0 |
| Sorbic acid | 96.0 |
| (0.1%) | 38.6 |
| sodium benzoate | 92.0 |
| (0.1%) | 36.2 |
| Free protamine | 31.0 |
| (0.1%) | 29.6 |
| Glycine (1%) + Free protamine | 65.6 |
| (0.1%) | 49.8 |
| Sodium acetate (0.4%) + | 58.4 |
| Free protamine (0.1%) | 40.2 |
| Lauric acid monoglyceride (0.01%) + | 50.2 |
| Free protamine (0.1%) | 38.6 |
| Ethanol (1%) + | 56.5 |
| Free protamine (0.1%) | 47.2 |
| Sorbic acid (0.1%) + | 110.2 |
| Free protamine (0.1%) | 70.8 |
| sodium benzoate (0.1%) + | 107.0 |
| free protamine (0.1%) | 68.5 |
| No addition | 21.5 |
| | 10.8 |

[1]Weight percent against the total weight of the specimens

In tests for the growth inhibition effect of various additives against Bacillus cereus, using a standard nutrient agar, emulsifying agents for food, such as caprylic acid monoglyceride, capric acid monoglyceride, and lauric acid monoglyceride, and phosphates, such as sodium polyphosphate and sodium hexametaphosphate, besides protamine, showed effectiveness. However, as shown by Example 4, in tests with actual food, cooked rice in the example, only protamine has proved to be effective. Whereas the above-mentioned substances were recognized as effective in tests on a laboratory basis, most of them failed to show effectiveness in tests with actual food. Sodium acetate and glycine rather than the above-mentioned substances have been proved effective, though the effect is of no practical value. It appears that actual foods contain some substances which act adversely upon the growth-inhibiting effect. Sodium acetate and glycine are considered to be fairly stable to the adverse influence. On the other hand, protamine exhibits an excellent effect in inhibition of growth of Bacillus cereus in tests with actual foods.

In Example 5 (potato salad was used), it has been discovered that additional use of glycine, sodium acetate, lauric acid monoglyceride, ethanol, sorbic acid, sodium benzoate, etc., in combination with protamine, markedly improves the growth inhibiting effect of protamine against Bacillus cereus.

A multiplication inhibitor provided according to the present invention is thus capable of preventing food poisoning caused by Bacillus cereus with marked effectiveness, and its introduction in industry will certainly be of high value.

What is claimed is:

1. A method of inhibiting multiplication of Bacillus cereus in processed foods, comprising adding an inhibitor composition comprising a Bacillus cereus multiplication inhibitor protamine or a salt thereof to processed food in an amount of 0.001 to 2 percent protamine by weight of the food, wherein inhibition of the multiplication of Bacillus cereus is effected without the addition of heat.

2. A method of inhibiting multiplication of Bacillus cereus in processed foods as recited in claim 1, wherein the processed food has been produced primarily from cereal.

3. A method of inhibiting multiplication of Bacillus cereus in processed foods as recited in claim 2, wherein said cereal consists of cooked rice.

4. A method of inhibiting multiplication of Bacillus cereus in processed foods as recited in claim 1, wherein the protamine is a free protamine.

5. A method of inhibiting multiplication of Bacillus cereus in processed foods as recited in claim 4, wherein the inhibitor composition further comprises sorbic acid.

6. A method of inhibiting multiplication of Bacillus cereus in processed foods as recited in claim 1, wherein the inhibitor composition further comprises an amino acid.

7. A method of inhibiting multiplication of Bacillus cereus in processed foods as recited in claim 1, wherein the inhibitor composition further comprises an emulsifying agent.

8. A method of inhibiting multiplication of Bacillus cereus in processed foods as recited in claim 1, wherein the inhibitor composition further comprises an organic acid or a salt of an organic acid.

9. A method of inhibiting multiplication of Bacillus cereus in processed foods as recited in claim 1, wherein the inhibitor composition further comprises an alcohol.

10. A method of inhibiting multiplication of Bacillus cereus in processed foods as recited in claim 1, wherein the inhibitor composition further comprises a phosphoric acid or a salt of a phosphoric acid.

11. A method of inhibiting multiplication of Bacillus cereus in processed foods as recited in claim 1, wherein the inhibitor composition further comprises an additive selected from the group consisting of glycine, sodium acetate, lauric acid monoglyceride, ethanol, sorbic acid and sodium benzoate.

12. A method of inhibiting multiplication of Bacillus cereus in processed foods as recited in claim 11, wherein the additive is in an amount approximately equal to the amount of protamine.

13. A method of inhibiting multiplication of Bacillus cereus in processed foods as recited in claim 1, wherein the inhibitor composition is added to the processed food at about room temperature.

* * * * *